United States Patent [19]

Fuhrmann et al.

[11] Patent Number: 5,030,771
[45] Date of Patent: Jul. 9, 1991

[54] METHOD OF PRODUCING ALIPHATIC AND CYCLOALIPHATIC DIOLS BY CATALYTIC HYDROGENATION OF DICARBOXYLIC ACID ESTERS

[75] Inventors: Werner Fuhrmann, Haltern; Günther Bub; Manfred zur Hausen, both of Marl, all of Fed. Rep. of Germany

[73] Assignee: Huels Aktiengesellschaft, Marl, Fed. Rep. of Germany

[21] Appl. No.: 453,970

[22] Filed: Dec. 20, 1989

[30] Foreign Application Priority Data

Dec. 24, 1988 [DE] Fed. Rep. of Germany ....... 3843956

[51] Int. Cl.⁵ ............................................. C07C 29/141
[52] U.S. Cl. ..................................... 568/814; 568/811; 568/830; 568/861; 568/864; 568/884; 568/885
[58] Field of Search ............... 568/814, 821, 822, 838, 568/839, 864, 885, 884, 861, 830, 326

[56] References Cited

U.S. PATENT DOCUMENTS

| | | | |
|---|---|---|---|
| 2,137,407 | 11/1938 | Lazier | 568/864 |
| 2,884,450 | 4/1959 | Holmquist | 568/864 |
| 4,268,695 | 5/1981 | Lange et al. | 568/864 |
| 4,361,710 | 11/1982 | Weitz et al. | 568/864 |
| 4,584,419 | 4/1986 | Sharif | 568/864 |
| 4,652,685 | 3/1987 | Cawse et al. | 568/864 |
| 4,751,334 | 6/1988 | Turner | 568/864 |

*Primary Examiner*—Werren B. Lone
*Attorney, Agent, or Firm*—Oblon, Spivak, McClelland, Maier & Neustadt, P.C.

[57] ABSTRACT

A method of producing aliphatic and cycloaliphatic diols by catalytic hydrogenation of dicarboxylic acid esters by the use of a copper chromite catalyst in which the copper content (calculated as CuO) is 40–47 wt. %, and the chromium content (calculated as $Cr_2O_3$) is 40–47 wt. %, and barium is also present in the amount of up to 10 wt. % (calculated as BaO) under mild temperature and pressure conditions is disclosed. The method produces diols without the formation of high boiling materials and does not require purification of the product diols by overhead distillation.

19 Claims, No Drawings

METHOD OF PRODUCING ALIPHATIC AND CYCLOALIPHATIC DIOLS BY CATALYTIC HYDROGENATION OF DICARBOXYLIC ACID ESTERS

BACKGROUND OF THE INVENTION

Field of the Invention

The present invention relates to a method of producing aliphatic and cycloaliphatic diols by catalytic hydrogenation of dicarboxylic acid esters.

Discussion of the Background

Cycloaliphatic and aliphatic α,ω-diols may be manufactured by the hydrogenation of the corresponding dicarboxylic acid esters. As catalysts for the hydrogenation, copper catalysts are preferably used, possibly with chromium and barium as promoters, and with or without a support. Other promoters which may be used include the alkaline earth metal, Ba, and alkali metals, such as Na and K. However, hydrogenation carried out with these catalysts, either in a liquid bath or in a trickling liquid, is not capable of achieving high selectivity for the desired diol, if high conversions are to be attained. Therefore, it is necessary to refine the crude product from the hydrogenation by distillation, in order to separate the components which boil at higher temperatures than the diols.

Thus, in European Patent 55 the production and use of a hydrogenation catalyst are described, in which aqueous solutions of salts of copper, nickel, and/or cobalt are mixed with alkali silicate solutions in a specified ratio, with the metal content of copper, nickel, and/or cobalt in the finished catalyst being 40-80 wt. %. In Example 1 of European Patent 55, diols are produced by hydrogenation using a copper catalyst over silica suspended in the amount of 5 wt. % in a mixture of the corresponding $C_4$-$C_6$-dicarboxylic acid methyl esters, at a mean temperature, $T_{mean}$, of 230° C. and a pressure of 250 bar. After a reaction time of 12 hr, the original ester number of 700 fell only to 60.

DE-PS 2,611,374, discloses catalysts for the hydrogenation of carboxylic acid esters to form the corresponding alcohols, which are comprised of copper, chromium, and alkali compounds, and possibly an alkaline earth metal and a support. It is specified that 0.3-0.7 g-atom of chromium per g-atom of copper must be used. Thus, for hydrogenation of an adipic acid hexanediol ester, dissolved 1:3 in 1,6-hexanediol, a Cu-CrNa catalyst is used, in a hydrogenation reactor at a $T_{mean}$ of 200° C. and a pressure of 250 bar, with a catalyst loading of 0.4 kg of mixture per liter of reaction space per hr, and a hydrogen throughput of 50 liter (STP) per liter of reaction space per hr, which results in practically complete conversion. However, on the basis of the dicarboxylic acid converted, the yield of 1,6-hexanediol is only 98.5-99%, with a distillation residue of 0.5-1%.

According to DE-PS 1,154,448, high molecular weight alcohols can be produced by catalytic hydrogenation of fatty acid esters by copper multialloy catalysts. For example, according to Example 3 of DE-PS 1,154,448, adipic acid di-n-butyl ester was hydrogenated to 1,6-hexanediol on a CuZnCr catalyst, with no carrier, at a $T_{mean}$ of 250° C. and a pressure of 220 bar, with a catalyst loading of 0.27 kg ester/liter/hr and a gas loading of 10,570 liter (STP) per liter catalyst per hr. With nearly complete conversion (ester number less than 3), after distillation a yield of 90-95% was obtained. Sebacic acid di-n-butyl ester was hydrogenated to 1,10-decanediol under the same conditions, with a yield of 90-95% of theoretical.

According to DE-PS 1,159,925, a copper/chromium/potassium hydrogenation catalyst on a silicic acid support is described, wherewith the silicic acid, of a wide pore type with a specified active surface, is impregnated with the appropriate compounds and is dried. The finished catalyst contains 18-30 wt. % copper, 0.3-3.5 wt. % chromium, and 0.5-9 wt. % potassium.

According to Example 1 of DE-PS 1,159,925, at a $T_{mean}$ of 215°-222° C., a pressure of 200 bar, a catalyst loading of 0.1 kg adipic acid di-ethylhexyl ester per liter catalyst per hr, and a gas loading of 282 liter hydrogen (STP) per liter catalyst per hr, with a CuCrK catalyst on a silica support, 1,6-hexanediol was obtained following distillation with nearly complete conversion (ester number=2) and a yield of 94.5% of theoretical. Hydrogenation of sebacic acid di-n-butyl ester (Example 1f) at a $T_{mean}$ of 220°-225° C., with the other conditions being the same, gave 1,10-decanediol following distillation with nearly complete conversion (ester number=3) and a yield of 96% of theoretical. Hydrogenation of hexahydroterephthalic acid di-n-butyl ester (Example 1d) at a $T_{mean}$ of 210° C. and a gas loading of 28.2 liter hydrogen (STP) per liter catalyst per hr, with the other conditions being the same, gave 1,4-di-hydroxymethylcyclohexane following distillation with nearly complete conversion (ester number=1) and a yield of 95% of theoretical.

DE-PS 1,202,269 discloses the production of 1,4-dihydroxymethylcyclohexane by catalytic hydrogenation of a terephthalic acid dialkyl ester to a hexahydroterephthalic acid dialkyl ester (first stage), on a palladium catalyst, and further hydrogenation to form the product (second stage), on a copper chromite catalyst. Suitable catalysts contain copper (CuO basis) in the amount of 30-80 wt. %, chromium ($Cr_2O_3$ basis) in the amount of 15-55 wt. %, and barium (BaO basis) in the amount of 0-15 wt. %.

In the Examples of DE-PS 1,202,269, the hydrogenation of hexahydroterephthalic acid dimethyl ester is described in which a catalyst comprised of copper chromite and a support is used which has the following composition:

Cu 33.2 wt. % (as CuO); Cr 38.0 wt. % (as $Cr_2O_3$); Ba 10.4 wt. % (as BaO); Na 3.5 wt. % (as $Na_2O$); and $SiO_2$ 9.5 wt. %.

For the ester hydrogenation at a $T_{mean}$ of 260°-270° C. and a pressure of ca. 380-390 bar, a conversion of 97% was reported, with the liquid reaction product mixture being 68 wt. % 1,4-dihydroxymethylcyclohexane. Correspondingly, for the hydrogenation of hexahydroterephthalic acid dibutyl ester carried out under the same conditions, practically complete conversion was reported, with the liquid reaction product mixture being 49.1 wt. % 1,4-dimethylcyclohexane. Since no data are given on the amounts of the gaseous carbon compounds formed, the maximum yield for the methyl ester is 94.4% of theoretical, and for the butyl ester, 96.8% of theoretical. The catalyst employed loses its activity after 2 months of service, due to the severe reaction conditions.

Thus, all of the known methods of catalytic hydrogenation of dicarboxylic acid esters to form diols exhibit drawbacks, such as the requirement of relatively severe reaction conditions, the loss of catalyst activity after relatively short operating times, and the need for refining by distillation because of the formation of high-boiling by-products (DE-PS 2,611,376).

SUMMARY OF THE INVENTION

Accordingly, one object of the present invention is to provide a method of producing diols by hydrogenating dicarboxylic acid esters, which avoids the above-mentioned disadvantages.

It is another object of the present invention to provide a method of producing diols by hydrogenating dicarboxylic acid esters which allows the highly selective formation of the diol products without formation of high-boiling by-products.

It is another object of the present invention to provide a method of producing diols by hydrogenating dicarboxylic acid esters which employs mild reaction conditions and results in a long operating life of the catalysts used.

These and other objects, which will become apparent during the course of the following detailed description, have been achieved by the discovery that catalytic hydrogenation of dicarboxylic acid esters by means of a copper chromite catalyst, in which dicarboxylic acid esters are hydrogenated with or without solvents, at a temperature of 120°–220° C. and a pressure of 50–400 bar, in the presence of hydrogen, with the use of a copper chromite catalyst wherein the copper content (calculated as CuO) is 40–47 wt. %, and the chromium content (calculated as $Cr_2O_3$) is 40–47 wt. %, and barium is also present in the amount of up to 10 wt. % (calculated as BaO); gives the diol as a pure bottoms product from the raw reaction product mixture, without the need for overhead distillation.

DETAILED DESCRIPTION OF THE PREFERRED EMBODIMENTS

According to the invention, the dicarboxylic acid ester is contacted with hydrogen at a temperature of 120°–220° C., preferably 160°–210° C., and a pressure of 50–400 bar, preferably 210–320 bar, in the presence of the copper chromite catalyst. The liquid loading (LHSV, liquid hourly space velocity) on the catalyst is in the general range of 0.1–0.7 $m^3$ of ester/$m^3$ of catalyst per hr, preferably 0.12–0.4 $m^3$ of ester/$m^3$ of catalyst per hour, and the gas loading (GHSV, gas hourly space velocity) is in the range of 1,000–6,000 $Nm^3$ of $H_2$/$m^3$ of catalyst per hr, preferably 2,500–6,000 $Nm^3$ of $H_2$/$m^3$ of catalyst per hr. Preferably, a trickling reaction configuration (low liquid loading, with a gas-filled reactor) is used, but a liquid bath configuration (liquid-filled reactor, with a low gas loading) is suitable.

The esters may be hydrogenated in either pure or dissolved form. For esters which are solid at ambient temperature, it is particularly recommended that they be mixed with a solvent which is a liquid at ambient temperature. A preferred solvent is the same alcohol compound which is being produced in the ester hydrogenation. Obviously, any solvent used should be inert under the hydrogenation conditions.

Although any suitable dicarboxylic acid ester may be used in the present invention, it is preferred that the diacid ester have up to 12 carbon atoms in the diacid portion and up to 4 carbon atoms in the alcohol portion. It is particularly preferred that the diacid ester have up to 6 carbon atoms in the diacid portion. Thus, suitable diacid esters include di-n-butyl adipate, the di-n-butyl ester of sebacic acid, and dimethyl hexahydroterephthalate. It is preferred that the diol produced by the present method is an $\alpha,\omega$-diol.

The present catalysts have a copper content (calculated as CuO) of 40–47 wt. %, and the chromium content (calculated as $Cr_2O_3$) is also 40–47 wt. %; the preferred figures are about 44 wt. % copper and about 44 wt. % chromium. The barium content (calculated as BaO) of the catalyst is up to 10 wt. %, and is preferably about 9 wt. %. Physical parameters of the copper chromite catalysts used are as follows: specific surface, 20–40 $m^2$/g; pore volume, 0.20–0.24 cc/g; and bulk density, 1.2–1.6 g/cc. The exterior shape of the catalyst depends on the reaction configuration used, and other process-specific details.

Because of the highly selective reaction system, the refining of the reaction product mixture of the hydrogenation does not require the cost intensive fractional distillation of the diol which has hitherto been required. It has been found, in connection with the present invention, that, surprisingly, there is so little formation of high-boiling by-products under the present hydrogenation conditions that all that is needed to refine the diol is to distill off the solvent and the alcohol produced in the ester hydrogenation, and to remove the process-specific low-boiling and medium-boiling products which are formed in small amounts. This distillation may be accomplished, e.g., by steam distillation (which may involve an azeotrope) from the solution comprising the raw hydrogenation reaction product mixture. Temperatures of 50°–200° C., preferably 100°–150° C., are used, with pressures of 2–500 mbar, preferably 10–160 mbar. For further purification of the diol, which has previously had any solvent, alcohol, or low-boiling and medium-boiling materials removed to a high degree, the product is treated with steam under mild conditions, and is dried in vacuum. The bottoms product recovered is the highly purified diol.

A suitable apparatus for carrying out the method is any heatable vessel with a stirring means and without a distillation head, but possibly with splash guard means, which can be operated under vacuum, using a vacuum pump. The refining can be carried out in a continuous-flow system or batchwise.

Other features of the invention will become apparent in the course of the following descriptions of exemplary embodiments which are given for illustration of the invention and are not intended to be limiting thereof.

EXAMPLES

EXAMPLE 1

Into a trickling bed reactor with a volume of 1,500 liter there was charged 2,380 kg of a copper chromite catalyst with Cu content (calculated as CuO) 44.9 wt. %, Cr content (calculated as $Cr_2O_3$) 45.8 wt. %, Ba content (calculated as BaO) 9.1 wt. %, and ($Al_2O_3$, $SiO_2$, and SrO) 0.2 wt. %. After reduction of the catalyst with a $H_2$/$N_2$ mixture, a liquid loading of 0.23 $m^3$ adipic acid di-n-butyl ester per $m^3$ catalyst per hr, a gas loading of 3,670 $m^3$ hydrogen (STP) per $m^3$ catalyst per hr, and a mean reaction temperature over the bed length $T_{mean}$ of 182° C. were established. An ester number of 0.15 was measured in the product outlet stream. After 10 days of operation, the catalyst activity became constant, with a loading of 0.2 $m^3$ ester/$m^3$ catalyst/hr, mean catalyst temperature over the bed length of $T_{mean}=192°$ C., and pressure 300 bar. The ester number in the raw product outlet stream which occurred under these conditions was between 0.1 and 0.2 mg KOH/g. The acid number was close to zero. A gc/ms analysis of the product outlet stream showed, in addition to an ester content corresponding to this ester number (0.1–0.2), only traces (less than 3,000 ppm) of components (ethers) boiling higher than 1,6-hexanediol.

After 40 days of operation, 284 metric tons of ester had been hydrogenated, and the activity and selectivity of the catalyst were undiminished.

The raw 1,6-hexanediol outlet stream produced by the hydrogenation of the adipic acid di-n-butyl ester (along with the added n-butanol) contained the following:

| | |
|---|---|
| 1,6-Hexanediol | 40.97 wt. % |
| n-Butanol | 58.43 wt. % |
| Prior eluate, intermediate eluate, and residue (total) | 0.60 wt. % |

The hydrogenation product outlet stream was continuously collected in a 35 m³ stirred vessel. The collected material was essentially free of solvent, because the n-butanol was distilled off at 125° C. and 50 mbar. The content of 1,6-hexanediol in the distillate was 0.3 wt. %. After about 50 metric tons of butanolic 1,6-hexanediol solution had been withdrawn, the feed to the reactor was interrupted. When a residual butanol content of less than 1 wt. % was reached, the vessel contents were subjected to steam stripping, by means of injection of water, with water in the amount of 5 wt. % (based on the amount of 1,6-hexanediol) being introduced in a period of 5 hr, under conditions of 115°–120° C. and 65 mbar. The distillate from the steam stripping, which contained 1,6-hexanediol in the amount of 1.5 wt. %, of the total 1,6-hexanediol present, which had been volatilized by the steam, was separately captured, collected, and sent to further processing. The bottoms product was dried at 110°–115° C. and 10 mbar. It comprised highly purified 1,6-hexanediol (greater than 99.9 wt. %). Other characteristics of the product were: solidification point, greater than 42° C.; water content, less than 0.1 wt. %, color, 5 APHA (American Public Health Association); and acid number less than 0.01 mg KOH/g.

The yield over all stages was 75.19 kg 1,6-hexanediol per 100 kg adipic acid fed, which is 92.98% of theoretical.

EXAMPLE 2

Into a trickling bed reactor with a volume of 5,000 liter there was charged 7,140 kg of the copper chromite catalyst described in Example 1. After reduction of the catalyst with a H₂/N₂ mixture, for hydrogenation of sebacic acid di-n-butyl ester, a liquid loading of 0.16 m³ of the mixture of the ester and n-butanol per m³ catalyst per hr, a gas loading of 4,000 Nm³ hydrogen per m³ catalyst per hr, and a mean catalyst temperature over the bed length, $T_{mean}$ of 185° C. were established when a steady state was reached, with pressure 300 bar. An ester number of between 0.1 and 0.25 mg KOH/g was measured in the product outlet stream. The acid number was close to zero. A gc-ms analysis of the product outlet stream gave, in addition to an ester content corresponding to the ester number, a content of components boiling higher than 1,10-decanediol of 2,000–4,000 ppm. The activity and selectivity of the catalyst remained constant.

The raw 1,10-decanediol outlet stream produced by the hydrogenation of the sebacic acid di-n-butyl ester contained, apart from the added n-butanol, the following:

| | |
|---|---|
| 1,10-Decanediol | 67.71 wt. % |
| n-Butanol | 31.27 wt. % |
| prior eluate, intermediate eluate, and residue (total) | 1.02 wt. % |

The raw 1,10-decanediol was refined and treated as described in Example 1. The operating conditions to achieve a residual butanol content of less than 0.5 wt. % in the bottoms were 130° C. (maximum) and 40 mbar. The bottoms were then steam stripped with addition of water in the amount of 5%, based on the amount of decanediol present. For this, $T_{mean}$ of 135° C. and a pressure of 60 mbar were established for 30 min. Then the product was dried at 150° C. and 20 mbar. After 1 hr, the water content was less than 0.1 wt. %. The bottoms product comprised highly purified 1,10-decanediol (greater than 99.3 wt. %). Other analytical data for the product were: color, 10 APHA; acid number, less than 0.01 mg KOH/g; and solidification point, 73° C.

The butanol recovered from the head product was 99.4% pure. It contained 1,10-decanediol in the amount of about 0.1 wt. %, in addition to small amounts of prior and intermediate eluate. The distillate from the steam distillation contained 1,10-decanediol in the amount of 3 wt. % based on the total 1,10-decanediol present.

EXAMPLE 3

Into a trickling bed reactor with a volume of 8,000 liter there was charged 12,066 kg of the copper chromite catalyst described in Example 1. After reduction of the catalyst with a H₂/N₂ mixture and establishment of a steady state in hydrogenation of adipic acid di-n-butyl ester, a liquid loading of 0.16 m³ of the mixture of the ester per m³ catalyst per hr, a gas loading of 2,000 Nm³ hydrogen per m³ catalyst per hr, and a mean catalyst temperature over the bed length, $T_{mean}$, of 170° C. were established.

In 63 days of hydrogenation, 1,612 metric tons of ester were passed over the catalyst, in the course of which the ester throughput was increased from 1,250 liter ester per hr to 1,300 liter ester per hr, and the mean catalyst temperature was reduced from 170° C. to 157° C. Over the entire series, the composition of the raw 1,6-hexanediol outlet stream did not change, but remained the same as given in Example 1. The ester number was about 0.1 mg KOH/g.

The refining was carried out in the same manner and with the same results as in Example 1. Over all stages, the "feed factor" (ratio of feed material to product recovered) was 1.33 tons adipic acid per ton 1,6-hexanediol.

EXAMPLE 4

Following the 1,6-hexanediol series of Example 3, and after thorough washing, hexahydroterephthalic acid dimethyl ester was hydrogenated under the same conditions as described in Example 3.

The hydrogenation was carried out at a liquid throughput of 1,000 liter ester/hr, a circulating gas amount of 18,000 Nm³ (STP)/hr, and a mean catalyst temperature, $T_{mean}$, of 190° C. The ester number and acid number in the reaction product stream were both zero. Only traces of components boiling higher than the two 1,4-di-hydroxymethylcyclohexane isomers were present.

In a plurality of batches, 164 metric tons raw product stream was collected for refining in a 35 m³ stirred vessel. The initial product mixture contained the added methanol, in addition to 1,4-di-hydroxymethylcyclohexane in the amount of 62 wt. %. During the collection the temperature in the heated vessel was gradually raised to 100° C., and the pressure was simultaneously decreased from 160 to 90 mbar, wherewith the methanol was distilled off. When a residual methanol content in the bottoms of 0.75 wt. % was reached, the temperature was increased to 150° C. At this temperature and a pressure of 120 mbar, a total of 1,800 liter water was introduced into the product over a period of 5.5 hr. Then drying was carried out over 3.5 hr at the same temperature and pressure.

The bottoms product comprised highly purified 1,4-dihydroxymethylcyclohexane (greater than 99.9 wt. %). The other characteristic properties of the product were: solidification point greater than 33° C.; water content, less than 0.1 wt. %; color 5 to 10 APHA; and acid number less than 0.01 mg KOH/g.

Obviously, numerous modifications and variations of the present invention are possible in light of the above teachings. It is therefore to be understood that within the scope of the appended claims, the invention may be practiced otherwise than as specifically described herein.

What is new and desired to be secured by Letters Patents of the United States:

1. A method of producing an aliphatic or cycloaliphatic diol, comprising: contacting a dicarboxylic acid ester at a temperature of 120°–220° C. and a pressure of 50–400 bar, in the presence of hydrogen, with a copper chromite catalyst, wherein said catalyst comprises copper in an amount, calculated as CuO, of 40–47 wt. %, chromium in an amount, calculated as $Cr_2O_3$, of 40–47 wt. %, and barium in an amount, calculated as BaO, up to 10 wt. %, wherein said catalyst has a specific surface of 20–40 m²/g, a pore volume of 0.2–0.24 cc/g, and a bulk density of 1.2–1.6 g/cc, and said contacting is carried out as a trickling reaction.

2. The method of claim 1, wherein said catalyst comprises copper in an amount of about 44 wt. %, chromium in an amount of about 44 wt. %, and barium in an amount of about 9 wt. %.

3. The method of claim 1, wherein any solvent, used in said contacting, and the alcohol, produced in said contacting, are removed from said diol by distillation.

4. The method of claim 3, wherein said distillation is carried out at a temperature of 50° to 200° C.

5. The method of claim 4, wherein said distillation is carried out at a temperature of 100° to 150° C.

6. The method of claim 3, wherein said distillation is carried out at a pressure of 2 to 500 mbar.

7. The method of claim 6, wherein said distillation is carried out at a pressure of 10 to 160 mbar.

8. The method of claim 1, wherein any process-specific low-boiling and intermediate-boiling materials are removed from said diol by steam distillation.

9. The method of claim 1, wherein said diol is purified by a steam treatment.

10. The method of claim 1, wherein said contacting is carried out with a liquid loading of 0.1–0.7 m³ of said ester per m³ of said catalyst per hour.

11. The method of claim 10, wherein said liquid loading is 0.12 to 0.4 m³ of said ester per m³ of said catalyst per hour.

12. The method of claim 1, wherein said contacting is carried out with a gas loading of 1,000–6,000 Nm³ of said hydrogen per m³ of said catalyst per hour.

13. The method of claim 12, wherein said gas loading is 2,500 to 6,000 Nm³ of said hydrogen per m³ of said catalyst per hour.

14. The method of claim 1, wherein said dicarboxylic acid ester is one member selected from the group consisting of adipic acid di-n-butyl ester, sebacic acid di-n-butyl ester, and hexahydroterephthalic acid dimethyl ester.

15. The method of claim 1, wherein said temperature is 160° to 210° C.

16. The method of claim 1, wherein said pressure is 210 to 320 bar.

17. The method of claim 1, wherein said dicarboxylic acid ester has up to 12 carbon atoms in the diacid portion and up to 4 carbon atoms in the alcohol portion.

18. The method of claim 1, wherein said dicarboxylic acid ester has up to 6 carbon atoms in the diacid portion.

19. The method of claim 1, wherein said diol is an $\alpha,\omega$-diol.

* * * * *